United States Patent [19]

Distler et al.

[11] 4,164,511
[45] * Aug. 14, 1979

[54] MANUFACTURE OF N-ARYLGLYCINONITRILES

[75] Inventors: Harry Distler, Bobenheim; Helmut Schlecht; Erwin Hartert, both of Ludwigshafen, all of Fed. Rep. of Germany

[73] Assignee: BASF Aktiengesellschaft, Fed. Rep. of Germany

[*] Notice: The portion of the term of this patent subsequent to May 10, 1994, has been disclaimed.

[21] Appl. No.: 792,696

[22] Filed: May 2, 1977

[30] Foreign Application Priority Data

May 14, 1976 [DE] Fed. Rep. of Germany ....... 2621450
May 15, 1976 [DE] Fed. Rep. of Germany ....... 2621728

[51] Int. Cl.$^2$ ................... C07C 120/00; C07C 121/78
[52] U.S. Cl. ................................................. 260/465 E
[58] Field of Search ............ 260/464, 465 E, 465.5 R, 260/465.5 A

[56] References Cited

U.S. PATENT DOCUMENTS 4,022,815  5/1977  Schlecht et al. .............. 260/465.5 A Primary Examiner—Joseph P. Brust
Attorney, Agent, or Firm—Keil & Witherspoon

[57] ABSTRACT

Manufacture of N-arylglycinonitriles by reacting N-arylamines with carbonyl compounds and hydrogen cyanide under specific reaction conditions in respect of the temperature, reaction time and hydrogen cyanide concentration.

The N-arylglycinonitriles obtainable by the process of the invention are antioxidants and valuable starting materials for the manufacture of dyes, fungicides, bactericides, textile assistants and as inhibitors for use in antifreezes.

15 Claims, No Drawings

MANUFACTURE OF N-ARYLGLYCINONITRILES

The present invention relates to a process for the manufacture of N-arylglycinonitriles by reacting N-arylamines with carbonyl compounds and hydrogen cyanide under specific reaction conditions in respect of the temperature, reaction time and hydrogen cyanide concentration.

German Pat. No. 656,350 discloses that glycollic acid nitrile can be reacted with excess methylamine in aqueous solution under pressure, to give sarcosinonitrile. An excess of up to 10 moles of methylamine per mole of hydroxyacetonitrile is recommended in order to achieve good yields of sarcosinonitrile (German Pat. No. 656,350). If stoichiometric amounts are used, considerable amounts of the nitrile of methyldiglycollamic acid are formed, and this compound is difficult to remove.

Another method of preparation of N-alkyl-substituted glycinonitriles uses formaldehyde, in the presence of sodium bisulfite compounds, as the starting material, the aldehyde being reacted with sodium cyanide and aliphatic amines. Using sodium cyanide and sodium bisulfite presents environmental problems when the method is carried out industrially, on account of the formation of alkali metal salts, which may contain residual cyanides, as by-products. The use of the amines in the form of salts, eg. hydrochlorides has also already been proposed (Jean Mathieu and Jean Weil-Raynal, Formation of C—C Bonds, volume I, pages 442-446 (Georg Thieme Verlag, Stuttgart 1973)).

All these methods are unsatisfactory from the point of view of simple and economical operation, good yields of end product and ease of working up and also in particular in respect of protection of the environment and purification of waste water.

German Laid-Open Application DOS 1,543,342 discloses the continuous reaction of aniline with formaldehyde and hydrogen cyanide at from 80° to 130° C., followed by hydrolysis of the reaction mixture with alkali metal hydroxide. Phenylglycinonitrile itself is not isolated. The patent application states that in general less than 10%, and frequently only from 1 to 5%, of the hydrogen cyanide and the formaldehyde are present in the free form in the reaction mixture. In none of the Examples is free hydrogen cyanide used.

We have found that N-arylglycinonitriles of the formula

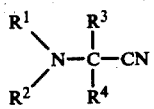
                  I where $R^1$, $R^2$, $R^3$ and $R^4$ may be identical or different and each is an aromatic radical, $R^3$ and $R^4$ may also each be hydrogen or an aliphatic, cycloaliphatic or araliphatic radical and $R^2$ may also be hydrogen, are obtained advantageously if N-arylamines of the formula

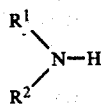
                  II where $R^1$ and $R^2$ have the above meaning, are reacted with carbonyl compounds of the formula

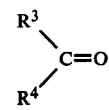
                  III where $R^3$ and $R^4$ have the above meaning, and hydrogen cyanide in the presence of water for from 0.1 to 4 hours at from 0° to 80° C., the concentration of hydrogen cyanide during the reaction being not more than 0.9% by weight, based on the reaction mixture.

Where aniline and formaldehyde are used, the reaction may be represented by the following equation:

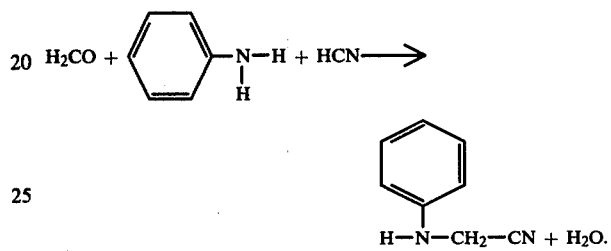

Compared with the process disclosed in German Laid-Open Application DOS 1,543,342, the process of the invention gives N-arylglycinonitriles more simply and more economically, in better yield and higher purity. The process is particularly suitable for operation on an industrial scale and for continuous operation, presents no substantial waste water problems and gives virtually no resinous by-products which, at fairly high reaction temperatures, are preferentially formed, due to the presence of formaldehyde. All these advantageous properties are surprising in view of the prior art.

Formaldehyde may be used in the liquid form or as a gas, but is in general used in the form of its aqueous solution, advantageously of from 10 to 50 percent strength by weight and preferably of from 30 to 40 percent strength by weight. Hydrogen cyanide may be used as the gas or, advantageously, in the liquid form or in aqueous solution. The starting amine II may be used preferably by itself or in solution, advantageously in an organic solvent. The use of solutions of from 40 to 60 percent strength by weight is advantageous. The three starting materials may be reacted in stoichiometric amounts, or with any of the components in excess; preferably the conditions correspond to an excess, over the stoichiometric amount, of from 0.1 to 5 moles of amine, preferably from 0.5 to 1 mole of amine, and/or from 0.01 to 0.1 mole of hydrogen cyanide per mole of carbonyl compound III. Preferred starting materials II and III and accordingly preferred end products I are those where $R^1$, $R^2$, $R^3$ and $R^4$ may be identical or different and each is phenyl or naphthyl, $R^3$ and $R^4$ may in addition each be hydrogen, alkyl of 1 to 20, preferably of 1 to 8, and especially of 1 to 4, carbon atoms, alkenyl of 2 to 20, preferably of 2 to 8, carbon atoms, cycyloalkyl of 5 to 8 carbon atoms or aralkyl of 7 to 12 carbon atoms, and $R^2$ may in addition be hydrogen. The above radicals may in addition be substituted by groups and/or atoms which are inert under the reaction conditions, eg. nitro, hydroxyl or cyano, or alkyl or alkoxy each of 1 to 4 carbon atoms, or chlorine or bromine which are substituents of a phenyl nucleus.

The following are examples of suitable starting materials III: formaldehyde, acetaldehyde, propionaldehyde, n-butyraldehyde, isobutyraldehyde, 2-methylbutyraldehyde, 2-ethylcapronaldehyde, n-valeraldehyde, isovaleraldehyde, 2,2-dimethylpropionaldehyde, 2,2-dimethyl-3-hydroxypropionaldehyde, n-capronaldehyde, iso-capronaldehyde, 2-methylvaleraldehyde, 3-methylvaleraldehyde, 2-ethylbutyraldehyde, 2,2-dimethylbutyraldehyde, 2,3-dimethylbutyraldehyde, 3,3-dimethylbutyraldehyde, enanthaldehyde, 2-methylcapronaldehyde, 3-methylcapronaldehyde, 4-methylcapronaldehyde, 5-methylcapronaldehyde, 2-ethylvalderaldehyde, 2,2-dimethylvaleraldehyde, 3-ethylvaleraldehyde, 3,3-dimethylvaleraldehyde, 2,3-dimethylvaleraldehyde, 4-ethylvaleraldehyde, 4,4-dimethylvaleraldehyde, 3,4-dimethylvaleraldehyde, 2,4-dimethylvaleraldehyde, 2-ethyl-2-methylbutyraldehyde, phenylacetaldehyde, acetone, methyl ethyl ketone, methyl n-propyl ketone, methyl isopropyl ketone, methyl n-butyl ketone, methyl sec.-butyl ketone, methyl tert.-butyl ketone, methyl n-pentyl ketone, methyl pentyl-2 ketone, methyl pentyl-3 ketone, methyl isoamyl ketone, methyl(2-methyl)-butyl ketone, methyl(1-methyl)-butyl ketone, methyl(2-ethyl)-butylketone, methyl(3-ethyl)-butyl ketone, methyl(2,2-dimethyl)-butyl ketone, methyl(2,3-dimethyl)-butyl ketone and methyl(3,3-dimethyl)-butyl ketone; corresponding unsymmetrical ketones which contain phenyl, benzyl, cyclohexyl, ethyl, n-propyl, isopropyl or n-butyl instead of methyl; diethyl ketone, di-n-propyl ketone, di-isopropyl ketone, di-n-butyl ketone, di-isobutyl ketone, di-sec.-butyl ketone, di-tert.-butyl ketone, di-n-pentyl ketone, dipentyl-2 ketone, dipentyl-3 ketone, diisoamyl ketone, di-(2-methyl)-butyl ketone, di-(1-methyl)-butyl ketone, di-(2-ethyl)-butyl ketone, di-(3-ethyl)-butyl ketone, di-(2,2-dimethyl)-butyl ketone, di-(2,3-dimethyl)-butyl ketone, di-(3,3-dimethyl)-butyl ketone, dicyclohexyl ketone, dibenzyl ketone and benzophenone.

Examples of suitable starting materials II are methyl-, ethyl-, n-propyl-, isopropyl-, n-butyl-, isobutyl-, sec.-butyl- and tert.-buty-α-naphthylamine and -β-naphthylamine, the alkyl substituent being in the 3-, 4-, 5-, 6-, 7-, 8- or 2- or 1-position, preferably in the 2-, 4- or 5-position; corresponding methyl, ethyl, n-propyl, isopropyl, n-butyl, isobutyl, sec.-butyl and tert.-butyl ethers of the α- and β-naphthylamines which have a hydroxyl group in the above positions; α- and β-naphthylamine disubstituted in the 3,4-, 4,5-, 4,8-, 5,8- or 6,7-position by methyl, ethyl, n-propyl, isopropyl, n-butyl, isobutyl-, sec.-butyl or tert.-butyl; corresponding dihydroxynaphthalenes in which 2 hydroxyl groups in the stated positions are etherified by the above alkyl groups; corresponding α- and β-napthylamines with 2 of the above radicals α- which are, however, different from one another, eg. 4-ethyl-8-ethoxy-2-naphthylamine and 4-methyl-5-methoxy-1-naphthylamine; 2-methylaniline, 3-methylaniline, 4-methylaniline, 2-methoxyaniline, 3-methoxyaniline, 4-methoxyaniline, 2,3-dimethylaniline, 3,4-dimethylaniline, 2,6-dimethylaniline, 3,5-dimethylaniline, 2,3-dimethoxyaniline, 3,5-dimethoxyaniline, 3,5-dimethoxyaniline, 2-ethylaniline, 3-ethylaniline, 4-ethylaniline, 2,3-diethylaniline, 3,4-diethylaniline, 2,6-diethylaniline, 3,5-diethylaniline, 2-ethoxyaniline, 3-ethoxyaniline, 4-ethoxyaniline, 2-n-propylaniline, 3-n-propylaniline, 4-n-propylaniline, 2,3-di-n-propylaniline, 3,4-di-n-propylaniline, 2,6-di-n-propylaniline, 3,5-di-n-propylaniline, 2-isopropylaniline, 3-isopropylaniline, 4-isopropylaniline, 2-butylaniline, 3-butylaniline, 4-butylaniline, 2-isobutylaniline, 3-isobutylaniline, 4-isobutylaniline, 2-tert.-butylaniline, 3-tert.-butylaniline, 4-tert.-butylaniline, 2,3-diethoxyaniline, 3,4-diethoxyaniline, 2,6-diethoxyaniline, 3,5-diethoxyaniline, 2,3,4-, 3,4,5-, 2,4,6-, 2,3,6- and 2,3,5-trimethylaniline, 2,3,4-, 3,4,5-, 2,4,6-, 2,3,6- and 2,3,5-trimethoxyaniline, 2,3,4-, 3,4,5-, 2,4,6-, 2,3,6- and 2,3,5-triethylaniline and 2,3,4-, 3,4,5-, 2,4,6-, 2,3,6- and 2,3,5-triethoxyaniline; anilines monosubstituted or polysubstituted in the above positions by hydroxyl, nitro, chlorine and/or bromine instead of the above alkyl substituents or together with the above alkyl substituents; and N-arylamines disubstituted by the above phenyl radicals and/or naphthyl radicals; diphenylamine, α-naphthylamine, β-naphthylamine, α- or β-naphthylamine substituted respectively in the 2- or 1-position, or in the 4-position, by methyl, ethyl or n-propyl, 2-methylaniline, 3-methylaniline, 4-methylaniline, 4-methylaniline, 2,3-dimethylaniline, 3,4-dimethylaniline and especially aniline are preferred.

The reaction is carried out at from 0° to 80° C., in general at between 0° and 80° C., advantageously from 40° to 80° C., preferably from 45° to 75° C. and especially from 50° to 70° C., under reduced pressure, superatmospheric pressure or, preferably, atmospheric pressure, batchwise or, preferably, continuously. Water is advantageously used in the form of aqueous formaldehyde solution and/or aqueous amine solutions and in addition water is formed in the reaction itself; a total of from 1 to 6, preferably from 3 to 4, moles of water, based on per mole of carbonyl compound III, may be used. Hydrogen cyanide is added to the starting mixture, before and during the reaction, in an amount such that the concentration of hydrogen cyanide, based on the reaction mixture during the reaction, does not exceed 0.9 percent by weight, and is in general from 0.01 to 0.9, advantageously between 0.01 and 0.9, preferably from 0.01 to 0.8 and more particularly from 0.01 to 0.7 percent by weight. The concentration of hydrogen cyanide, based on the reaction mixture during the reaction, particularly preferentially does not exceed 0.1 percent by weight and is preferably from 0.01 to 0.1 and especially from 0.05 to 0.1 percent by weight. The reaction time (or, in continuous operation, the residence time) is from 0.1 to 4 hours, preferably from 1 to 2 hours. The use of water as the sole solvent is preferred, but organic solvents which are inert under the reaction conditions may also be present. Examples of suitable solvents are aromatic hydrocarbons, eg. toluene, benzene, ethylbenzene, o-, m- and p-xylene, isopropylbenzene and methylnapthalene; aliphatic or cycloaliphatic hydrocarbons, eg. heptane, α-pinene, pinane, nonane, gasoline fractions within a boiling range of from 70° to 190° C., cyclohexane, methylcyclohexane, petroleum ether, decalin, hexane, naptha, 2,2,4-trimethylpentane, 2,2,3-trimethylpentane, 2,3,3-trimethylpentane and octane; and corresponding mixtures. The solvent is advantageously used in an amount of from 40 to 10,000 percent by weight, preferably from 50 to 1,500 percent by weight, based on starting material III.

The reaction may be carried out as follows: a mixture of the carbonyl compound III, hydrogen cyanide and starting amine II, with or without water and/or organic solvent, is kept at the reaction temperature for the reaction time. Some of the hydrogen cyanide is introduced into the starting mixture and some is added during the reaction, in portions or continuously, so that the above concentration of hydrogen cyanide is maintained during the entire reaction time. The continuous measurement of the hydrogen cyanide concentration is advantageously carried out by means of a silver/calomel electrode. The end product is then isolated from the reaction mixture by conventional methods, eg. by distillation or by extraction, eg. with cyclohexane, followed by distillation of the solvent.

The N-arylglycinonitriles obtainable by the process of the invention are antioxidants and valuable starting materials for the manufacture of dyes, fungicides, bactericides, textile auxiliaries and inhibitors for use in antifreezes. Alkali metal salts of phenylglycine are used as starting materials for the synthesis of indigo. With regard to the use of the compounds, reference may be made to the above German Laid-Open Application and to Ullmanns Encyklopadie der technischen Chemie, volume 9, page 388, volume 15, page 219, and volume 19, pages 300, 317 and 339.

In the Examples which follow, parts are by weight.

EXAMPLE 1

Per hour, 400 parts of 30 percent strength by weight aqueous formaldehyde solution, 108 parts of liquid hydrogen cyanide and 372 parts of aniline are slowly mixed in a stirred kettle at 65° C.; the hydrogen cyanide concentration in the reaction space does not exceed 0.9 percent by weight (based on the reaction mixture), and averages 0.8 percent by weight. After a mean residence time of 60 minutes, the reaction mixture is passed into a reactor which is at 65° C. The mean residence time in the reactor is 45 minutes and the average hydrogen cyanide concentration is 0.5 percent by weight. Per hour, 880 parts of a reaction mixture are obtained; this is extracted with benzene and after evaporation of the benzene gives, per hour, 512 parts (98% of theory) of phenylglycinonitrile of $n_D^{50} = 1.5591$ and melting point 40°–42° C. (after recrystallization from a 1:1 mixture of cyclohexane and isopropanol).

EXAMPLE 2

Per hour, 400 parts of 30 percent strength by weight aqueous formaldehyde solution, 108 parts of liquid hydrogen cyanide and 372 parts of aniline are slowly mixed in a stirred kettle at 65° C.; the hydrogen cyanide concentration in the reaction space does not exceed 0.1 percent by weight (based on the reaction mixture), and averages 0.08 percent by weight. After a mean residence time of 60 minutes, the reaction mixture is passed into a reactor which is at 65° C. The mean residence time in the reactor is 45 minutes and the average hydrogen cyanide concentration is 0.04 percent by weight. Per hour, 880 parts of a reaction mixture are obtained; this is extracted with benzene and after evaporation of the benzene gives, per hour, 512 parts (98% of theory) of phenylglycinonitrile of $n_D^{50} = 1.5591$ and melting point 40°–42° C. (after recrystallization from a 1:1 mixture of cyclohexane and isopropanol).

We claim:

1. A process for the manufacture of an N-arylglycinonitrile of the formula

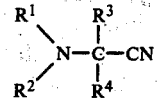

wherein
$R^1$, $R^2$, $R^3$ and $R^4$ each is an aromatic radical selected from the group consisting of phenyl and napthyl, $R^3$ and $R^4$ may also each be selected from the group consisting of hydrogen, alkyl of 1 to 20 carbon atoms, alkenyl of 2 to 20 carbon atoms, cycloalkyl of 5 to 8 carbon atoms and aralkyl of 7 to 12 carbon atoms, and $R^2$ may also be hydrogen, with the proviso that each of $R^1$, $R^2$, $R^3$ and $R^4$ other than hydrogen may also be further substituted by a group or atom which is inert under the reaction conditions, which process comprises:
reacting an N-arylamine of the formula

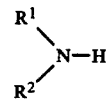

where
$R^1$ and $R^2$ have the above meaning, with a carbonyl compound of the formula

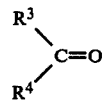

where
$R^3$ and $R^4$ have the above meaning, and with hydrogen cyanide in the presence of water for from 0.1 to 4 hours at from 0° to 80° C., the concentration of hydrogen cyanide during the reaction being not more than 0.9% by weight, based on the reaction mixture.

2. A process as claimed in claim 1, in which the reaction is carried out with an excess, over the stoichiometric amount, of from 0.1 to 5 moles of amine per mole of compound III.

3. A process as claimed in claim 1, in which the reaction is carried out with an excess, over the stoichiometric amount, of from 0.5 to 1 mole of amine per mole of compound III.

4. A process as claimed in claim 1, in which the reaction is carried out with an excess, over the stoichiometric amount, of from 0.01 to 0.1 mole of hydrogen cyanide per mole of compound III.

5. A process as claimed in claim 1, in which the reaction is carried out at from 0° to 80° C.

6. A process as claimed in claim 1, in which the reaction is carried out at from 40° to 80° C.

7. A process as claimed in claim 1, in which the reaction is carried out from 45° to 75° C.

8. A process as claimed in claim 1, in which the reaction is carried out at from 50° to 70° C.

9. A process as claimed in claim 1, in which the reaction is carried out with a total amount of from 1 to 6 moles of water per mole of carbonyl compound III.

10. A process as claimed in claim 1, in which the reaction is carried out with a concentration, during the reaction, of from 0.01 to 0.9 percent by weight of hydrogen cyanide, based on the reaction mixture.

11. A process as claimed in claim 1, in which the reaction is carried out with a concentration, during the reaction, of from 0.01 to 0.7 percent by weight of hydrogen cyanide, based on the reaction mixture.

12. A process as claimed in claim 1, in which the reaction is carried out with a concentration, during the reaction, of not more than 0.1 percent by weight of hydrogen cyanide, based on the reaction mixture.

13. A process as claimed in claim 1, in which the reaction is carried out with a concentration, during the reaction, of from 0.01 to 0.1 percent by weight of hydrogen cyanide, based on the reaction mixture.

14. A process as claimed in claim 1, in which the reaction is carried out with a concentration, during the reaction, of from 0.05 to 0.1% by weight of hydrogen cyanide, based on the reaction mixture.

15. A process as claimed in claim 1, in which the reaction is carried out for from 1 to 2 hours.

* * * * *